(12) United States Patent
Smith et al.

(10) Patent No.: US 10,173,026 B2
(45) Date of Patent: Jan. 8, 2019

(54) INFANT CALMING AID

(75) Inventors: Dean Maxwell Smith, Auckland (NZ); Mark Vincent Hubble, Auckland (NZ); Jason Paul Rogers, Auckland (NZ)

(73) Assignee: Gro-Group International Limited, Exeter (GB)

( * ) Notice: Subject to any disclaimer, the term of this patent is extended or adjusted under 35 U.S.C. 154(b) by 62 days.

(21) Appl. No.: 13/880,208

(22) PCT Filed: Oct. 21, 2011

(86) PCT No.: PCT/NZ2011/000223
§ 371 (c)(1),
(2), (4) Date: Jul. 8, 2013

(87) PCT Pub. No.: WO2012/053913
PCT Pub. Date: Apr. 26, 2012

(65) Prior Publication Data
US 2013/0296636 A1    Nov. 7, 2013

(30) Foreign Application Priority Data
Oct. 21, 2010   (NZ) .................................... 588751

(51) Int. Cl.
*A61M 21/02* (2006.01)
*A61M 21/00* (2006.01)

(52) U.S. Cl.
CPC ..... *A61M 21/02* (2013.01); *A61M 2021/0027* (2013.01); *A61M 2210/083* (2013.01); *A61M 2240/00* (2013.01)

(58) Field of Classification Search
CPC .................. A61M 21/00; A61M 21/02; A61M 2021/0005; A61M 2021/0027; A63H 3/00; A63H 3/003; A63H 3/14; A63H 3/28
USPC ...................................................... 600/26–28
See application file for complete search history.

(56) References Cited

U.S. PATENT DOCUMENTS

| | | |
|---|---|---|
| 4,635,516 A | 1/1987 | Giannini |
| 4,681,096 A | 7/1987 | Cuervo |
| 4,692,748 A | 8/1987 | Pinsak et al. |
| 4,777,938 A * | 10/1988 | Sirota ............................. 600/27 |
| 4,819,471 A | 4/1989 | Cook |
| 4,819,616 A | 4/1989 | Samson |

(Continued)

FOREIGN PATENT DOCUMENTS

| | | |
|---|---|---|
| CN | 2603637 Y | 2/2004 |
| GB | 1165541 | 10/1969 |

(Continued)

OTHER PUBLICATIONS

Machine translation (via EPO and Google) of Nonoyama (JP 2005196092).*

(Continued)

*Primary Examiner* — Thaddeus Cox
(74) *Attorney, Agent, or Firm* — Olson & Cepuritis, Ltd.

(57) ABSTRACT

An infant pacifying apparatus which includes: sound system includes a sound generator and associated power source; an auditory output device associated with the sound system; a receiving portion is configured to: be located on a hand or an arm of an adult cradling an infant; and house or be connected to a housing for containing: the auditory output device; or the sound system and auditory output device.

10 Claims, 7 Drawing Sheets

(56) References Cited

U.S. PATENT DOCUMENTS

| | | | |
|---|---|---|---|
| 5,520,616 A * | 5/1996 | Hofmeister | A61H 23/0263 128/898 |
| 7,346,949 B2 * | 3/2008 | Kamrin-Balfour | 5/655 |
| 2004/0121702 A1 | 6/2004 | Seibert et al. | |
| 2007/0083979 A1 | 4/2007 | Daniels | |
| 2007/0099680 A1 * | 5/2007 | Kielland | 455/575.1 |
| 2007/0101479 A1 | 5/2007 | Turner | |
| 2007/0161479 A1 | 7/2007 | Harris | |
| 2008/0137898 A1 | 6/2008 | Nenner | |
| 2009/0074224 A1 | 3/2009 | Wright | |
| 2009/0128343 A1 | 5/2009 | Wu | |
| 2009/0274323 A1 | 11/2009 | Godart | |
| 2009/0293166 A1 * | 12/2009 | Shayne | G06Q 30/02 2/20 |
| 2010/0093251 A1 * | 4/2010 | Viniotis | 446/295 |

FOREIGN PATENT DOCUMENTS

| | | | |
|---|---|---|---|
| GB | 2417426 | | 3/2006 |
| GB | 2481116 A | | 12/2011 |
| JP | H11164761 | * | 6/1999 ............... A47G 9/00 |
| JP | 2005196092 A | | 7/2005 |
| JP | 2007288745 A | | 11/2007 |
| JP | 2009207750 A | | 9/2009 |
| TW | M266837 U | | 6/2005 |
| WO | 96/04053 | | 2/1996 |
| WO | 2010010553 | | 6/2004 |

OTHER PUBLICATIONS

Machine translation (via EPO and Google) of Kosugi.*
European Search Report from co-pending EP Application 11 83 4694, dated May 4, 2015.
Japanese Office Action in Japanese Application No. 2013-534849 dated Sep. 28, 2015 and English translation.
Australian Examination Report in Australian Application No. 2015264806 dated Feb. 17, 2017.
Japanese Office Action in Japanese Application No. 2011800509586 dated Jan. 5, 2017 and English translation.
Australian Examination Report No. 2 in Australian Application No. 2015264806 dated Feb. 16, 2018.
Canadian Office Action in Application No. 2,853,123 dated Nov. 22, 2017.

* cited by examiner

INFANT CALMING AID

STATEMENT OF CORRESPONDING APPLICATIONS

This application is based on the Provisional specification filed in relation to New Zealand Patent Application Number 588751, the entire contents of which are incorporated herein by reference.

TECHNICAL FIELD

The present invention relates to an infant calming aid. In particular an infant calming aid which makes use of white noise or the like to soothe and pacify an infant.

BACKGROUND ART

Devices which make use of white noise to induce sleep in adults and to soothe and pacify infants are well known and a few representative examples include:
GB 1,165,541 Titled: Sleep Inducing Device.
This specification discloses a sine wave oscillator inside a pillow which can generate white noise.
U.S. Pat. No. 4,681,096 Titled: Method and Apparatus for Therapeutic Motion and Sound Treatment of Infants
This specification discloses an apparatus which imparts a rhythmic cyclic motion to a support surface as well as generate a sound at 60-80 decibels within a frequency range of 200 Hz and 4000 Hz.
U.S. Pat. No. 4,819,616 Titled: Baby Calmer
This specification details a sound source which generates a random noise over an audio frequency range to at least 10 kHz.
U.S. Pat. No. 4,825,471 Titled: Garment Useful for listening to Audio Signals
This specification discloses a garment to be worn on the upper torso of a human.

However, conventional infant calming devices employing white noise such as those outlined above suffer from one or more of the following drawbacks:
being bulky and not easily carried such as pillow;
being affixed to a support surface such as a cot;
needing to be worn by the infant which can be uncomfortable, impractical or dangerous in some situations or unsightly;
being designed for use within a cot or bassinet and not being readily portable;
producing a sound that is dangerously loud if the infants ear is positioned too close to the device;
not producing a sound in a region substantially adjacent an infant's ear;
producing a sound which is audible to adults in the vicinity of the device;
not permitting the adult holding the device in use to safely or confidently hold the infant at the same time, or to maintain tactile contact with the infant while in use
not being readily adaptable to a variety of different situations in which an infant may need to be calmed.

It is desirable for the present invention to address the foregoing problems or at least to provide the public with a useful choice.

Further aspects and advantages of the present invention will become apparent from the ensuing description which is given by way of example only.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

Throughout this specification, the word "comprise", or variations thereof such as "comprises" or "comprising", will be understood to imply the inclusion of a stated element, integer or step, or group of elements integers or steps, but not the exclusion of any other element, integer or step, or group of elements, integers or steps.

SUMMARY OF INVENTION

The present invention in essence relates to an infant calming apparatus which is worn on a person's hand or arm. The apparatus includes one or more contrivances which can generate white noise or other sounds to pacify an infant whose head is being cradled by the hand or arm of a person wearing the apparatus. The sound generating contrivances deliver sound to the ear of an infant yet preferably do not:
interfere with the comfort of the infant resting on the hand of the person wearing the apparatus; nor
substantially interfere with any normal tactile feedback provided to the wearer of the apparatus so as to indicate a hand or arm has made or is in contact with an infant's head.

The term "white noise" is sometimes defined as "a noise produced by a stimulus containing all of the audible frequencies of vibration." However, as used herein, the term "white noise" is used in a broader sense, and includes other heterogeneous mixtures of sound waves occurring over a wide frequency range, such as "pink noise" and "Gaussian noise." Thus, the term "white noise" also includes:
certain music melodies;
radio noise;
sounds that replicate the sounds in the womb such as a mother's heartbeat, and
sounds similar to those found in nature, such as the sounds of waves, wind, rain and waterfalls;
as well as the collective sounds of animals.
These sounds can be either naturally or artificially produced.

According to a first aspect there is provided an infant pacifying apparatus which includes:
a) a sound system comprising a sound generator and associated power source;
b) an auditory output device associated with the sound system;
characterised in that the apparatus includes:
a receiving portion (RP) which is configured to:
a) be located on a hand or an arm; and
b) house or be connected to a housing for containing:
the auditory output device; or
the sound system and auditory output device.

In some embodiments, the apparatus may also include a cover or pocket covering the sound system and sound output device which is either:
made from a substantially sound permeable material; and/or
is adapted to permit the permeation of sound through the RP.

According to a further aspect there is provided an infant pacifying apparatus substantially as described above wherein the RP is configured to house:
the auditory output device; or
sound system and sound output device;
in a manner which does not substantially interfere, in use, with the support and/or comfort of an infant's head.

According to a further aspect of the present invention there is provided an infant pacifying apparatus substantially as described above wherein the sound system and/or auditory output device is/are configured to enable the auditory output device to produce sound at a level, which can be heard by an infant being cradled, yet cannot be heard by an adult outside a radius of substantially 30 mm of the auditory output device.

According to a further aspect of the present invention there is provided an infant pacifying apparatus substantially as described above wherein the sound system and/or auditory output device is/are configured to enable the auditory output device to produce sound at a level which may audible to an adult cradling an infant but is not audible to any other adult within a 1 meter radius of the user.

In some embodiments of this aspect the sound is produced at a level of around 35-60 dB to ensure it is at a safe level for the child and not so loud as to be heard by the adult cradling the child unless the child is being held up close to the adult's face.

According to another aspect of the present invention there is provided an infant pacifying apparatus as claimed in any one of claims 3-5 wherein the sound is white noise.

According to a still further aspect of the present invention there is provided an infant pacifying apparatus substantially as described above wherein the RP is configured so that the sound system is positioned to not substantially interfere, in use, with:
a palm; and/or,
thumb and fingers; and/or
an arm;
of a user receiving tactile feedback: when moving to cradle, or when cradling, the infant's head.

According to a still further aspect of the present invention there is provided a method of pacifying an infant characterized by the step of:
a) using a sound system to deliver sounds to an associated auditory output device located on a palm or other part of an arm against which an infant's head can be cradled.

A method substantially as described above characterized by the further step of:
b) using the sound system and associated auditory output device to produce sound at a level, which can be heard by an infant being cradled yet cannot be heard by an adult outside a radius of substantially 30 mm of the auditory output device.

Several embodiments of the invention and advantages it provides will be further described in more detail below.

BEST MODES AND ILLUSTRATIVE EXAMPLES

Figure 1:
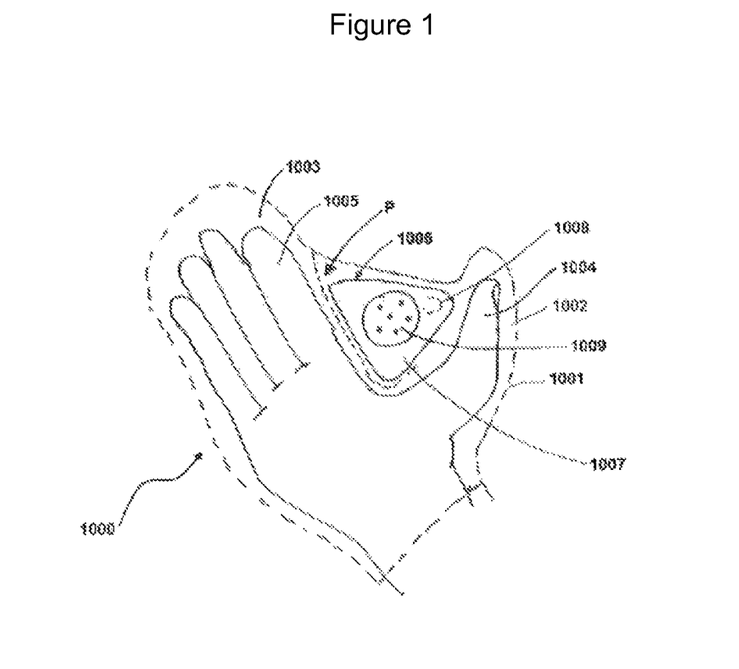
FIG. 1 shows a schematic plan view of the present invention in accordance with one embodiment.
Figure 2:
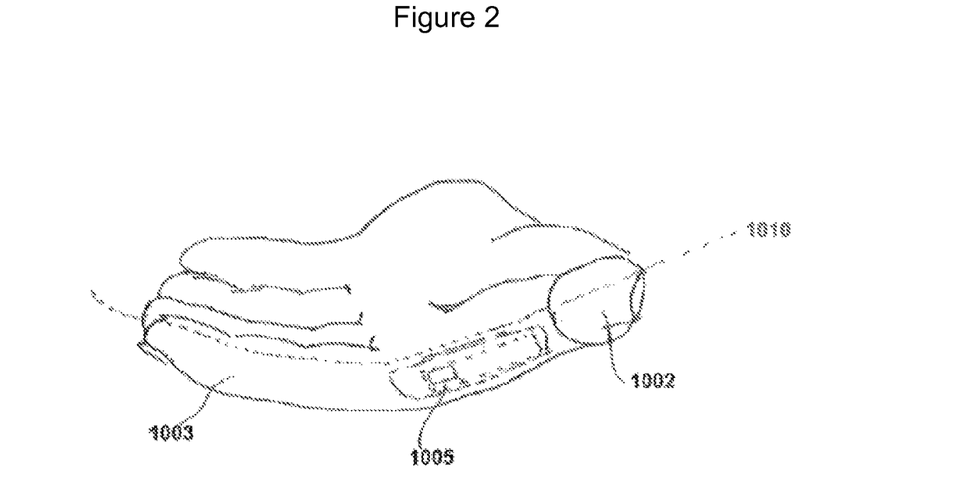
FIG. 2 shows a side view of FIG. 1.

With respect to FIGS. 1 and 2 there is provided an infant pacifying apparatus 1000 which has a receiving portion (RP) in the form of a mitten 1001 which has a thumb receiving portion 1002 and finger and palm receiving portion 1003. In one embodiment depicted mitten 1001 is made out of neoprene.

The mitten has located in a pocket P a sound system 1006 which has a sound generator 1007 and associated power source in the form of a rechargeable battery pack 1008 and speaker 1009. The pocket P is situated so that in use it is positioned between the thumb 1004 and index finger 1005 of a user. The pocket may have a re-sealable entrance (not shown) which uses fasteners such as domes or VELCRO™ strips (not shown).

In FIG. 2 it can be seen that the sound generator 1007 is positioned beneath the surface of the thumb, palm and fingers as indicated by dotted line 1010.

Figure 3:
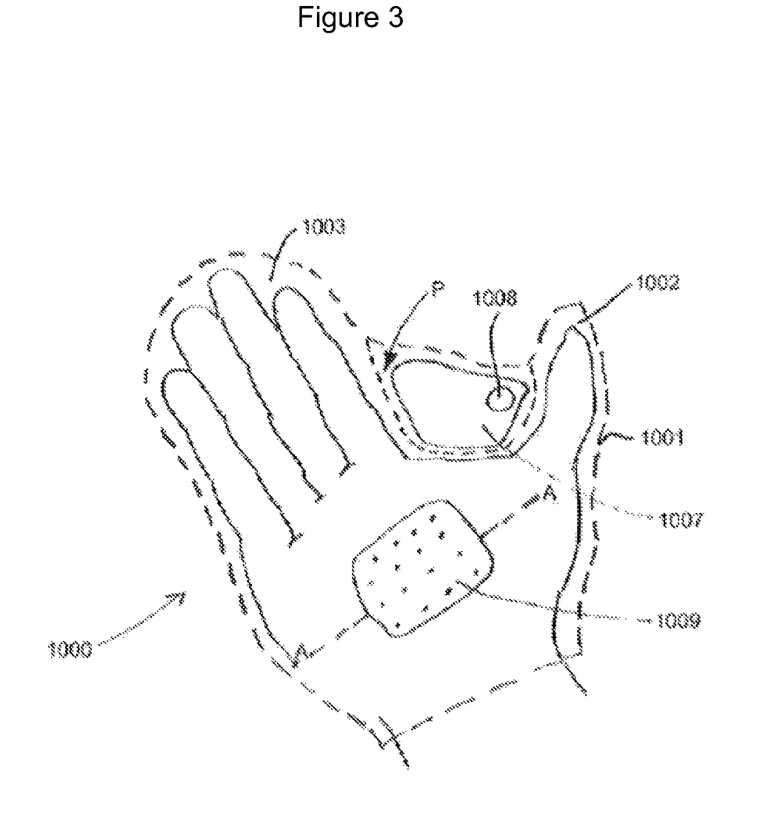
FIG. 3 shows a schematic plan view of an alternate embodiment of the present invention.
Figure 4:
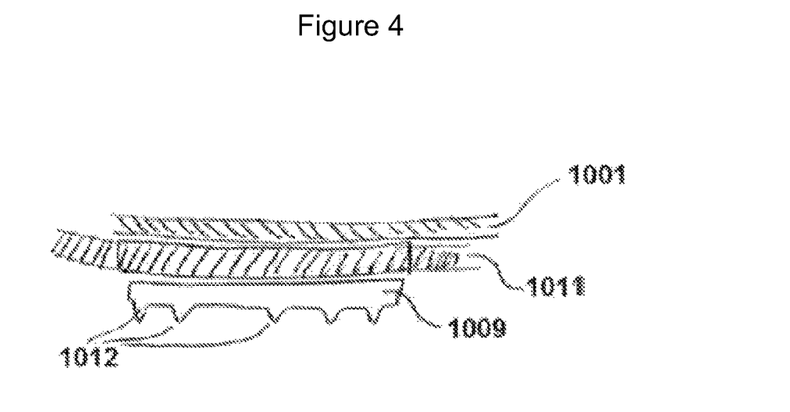
FIG. 4 shows a schematic cross sectional view along line A-A of FIG. 3.

In relation to FIGS. 3 and 4 there is shown an alternate embodiment with like elements to FIGS. 1 and 2 being represented with like reference numerals. The key difference with this embodiment is that the speaker 1009 is located remote to the sound system 1006 and is connected thereto by wires (not shown) or through a wireless connection, such as a BLUETOOTH connection, to a speaker 1009 which is a thin flexi speaker (such as a Flexpeaker™ developed by Taiwan's Technology Research Institute (ITRI)). The speaker 1009 is located under a foam layer 1011 which provides a cushion so the speaker does not interfere with the comfort of the baby. The speaker 1009 is optimally adapted to have tactile projections 1012 on the underside thereof which press against the palm of a user wearing the mitten 1001 to provide a tactile indicator as to when the mitten begins to support a baby's head.

Figure 5:
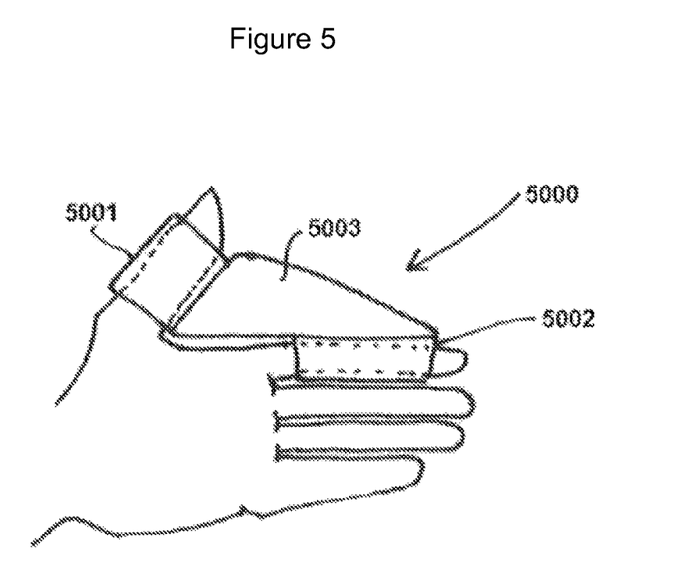
FIG. 5 shows a schematic view of a still further embodiment of the present invention.

In FIG. 5 there is shown another embodiment of an infant pacifying apparatus 5000 which has an RP in the form of a thumb receiving sleeve 5001 and finger sleeve 5002 with a web element 5003 connecting the sleeves 5001 and 5002. The web element 5003 is made out of neoprene and has a pocket therein (not shown) which houses the sound system (also not shown). The pocket has a re-sealable entrance (not shown) which uses fasteners such as domes or VELCRO™ strips (not shown).

Figure 6:
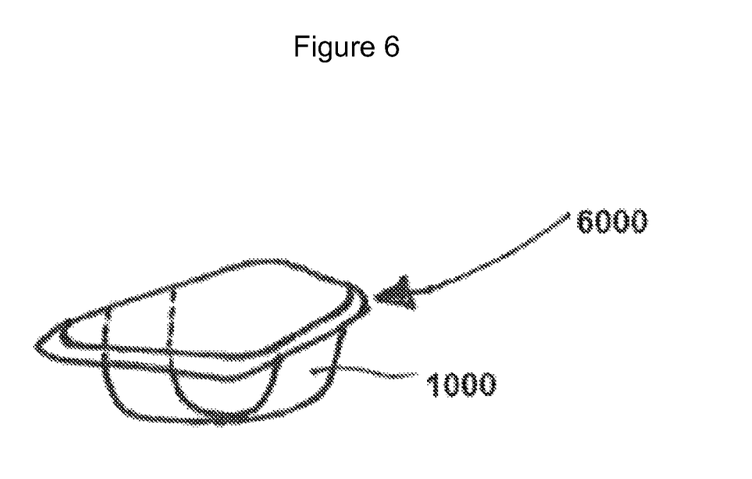
FIG. 6 shows a schematic view of yet another embodiment of the present invention.

In FIG. 6 there is shown an infant pacifying apparatus 6000 having an RP in the form of a mit 6000 made of neoprene. The mit 6000 has an elasticized band 6001 which together with the underside of the mit 6000 forms the RP.

The mit 6000 includes a pocket (not shown) which is accessed on the underside of the mit. The pocket houses the sound system (not shown).

Figure 7:
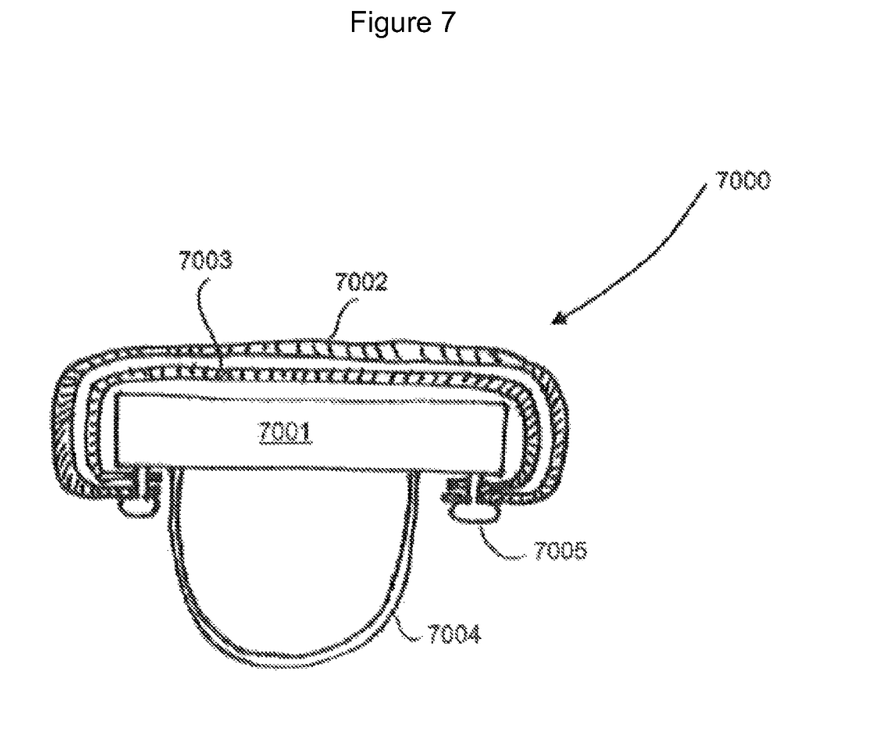
FIG. 7 shows a schematic side view of a variant embodiment of that shown in FIG. 6 which has interchangeable cushioning material.

In FIG. 7 there is shown an infant pacifying apparatus a mit 7000 which has a housing 7001 in which the sound system (not shown) is located. Interchangeable neoprene cushioning layers 7002 and 7003 cover the top surface of the housing 7001 on which an infant's head will be cradled. The mit 7000 has an elasticized band 7004 which together with the underside of the housing forms the RP. The cushioning layers include holes adjacent the four corners thereof which stretch over a bulbous headed male projections 7005 located on the underside of the housing 7001 near the corners thereof. The layers 7002 and 7003 provide the ability to remove a layer which has become wet and/or dirty whilst the wearer is out and about.

Figure 8:
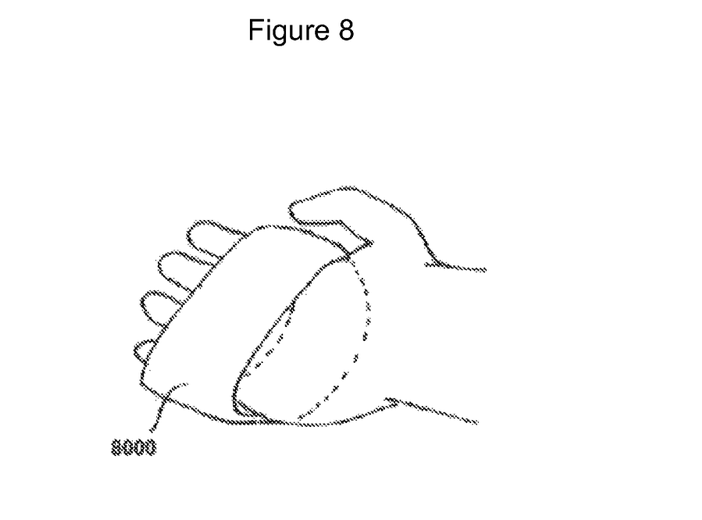
FIG. 8 shows a schematic view of a band according to one aspect of the present invention.
Figure 9:
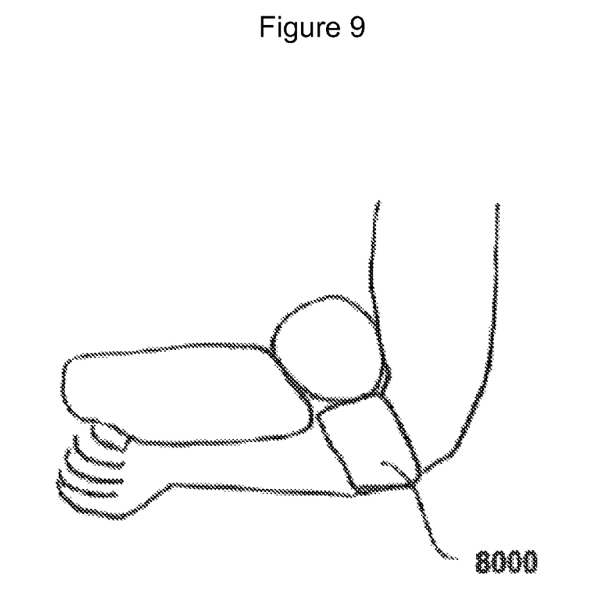
FIG. 9 shows a schematic view of a band as shown in FIG. 8 but worn on the arm of the user.

In FIG. 8 there is shown an RP in the form of a band 8000 made of an elasticized material similar to that used to tennis wrist bands. The band 8000 has a pocket (not shown) housing a sound system (not shown). The top of the pocket has cushioning in the form of a neoprene pad to cushion the infants head whilst resting on the sound system. The band 8000 may also stretch over the hand so as to be capable of being used in the crook of a person's elbow, as shown in FIG. 9.

Figure 10:
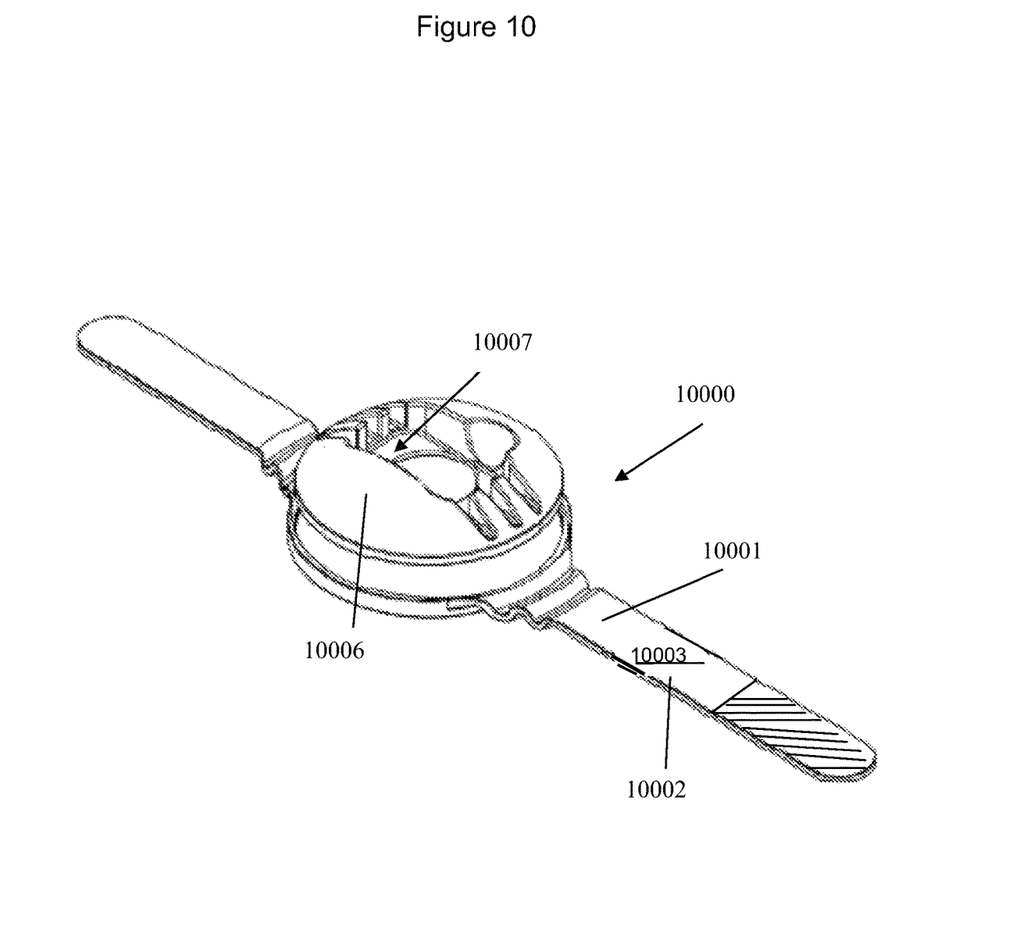
FIG. 10 shows a top perspective view of an alternate embodiment of the present invention.
Figure 11:
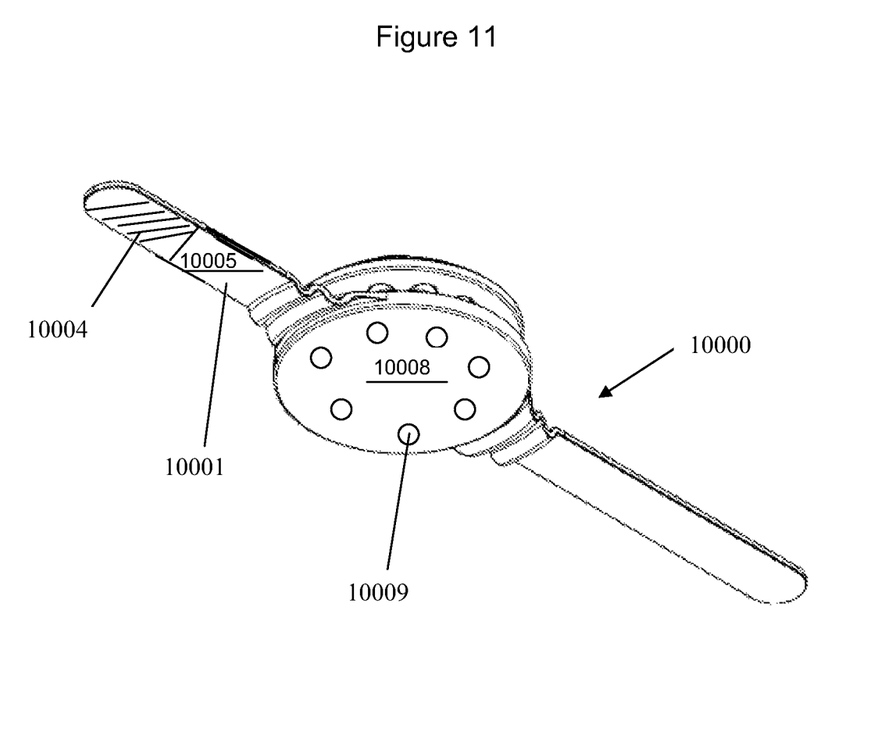
FIG. 11 shows a bottom perspective of the embodiment shown in FIG. 10.

In FIG. 10 and FIG. 11 there is shown an infant pacifying apparatus 10000 having an RP in the form of a strap 10001 which has Velcro hooks 10002 at one end thereof on a first surface 10003 of the strap 10001 and has Velcro loops 10004 at the other end thereof on a second surface 10005 of the strap 10001. The strap is connected via adhesive to a housing 10006 which houses an mp3 player (not shown) in a snug gripping cavity 10007 the mp3 player connects via Bluetooth to a speaker 10008. In use the strap is fitted around a person's hand so that the speaker 10008 is exposed and the mp3 and housing 10006 is adjacent the surface of a person's hand. The speaker 10008 is preferably surrounded by a foam covering (not shown).

An alternative arrangement that can be employed in relation to the infant pacifying apparatus 10000 shown in FIGS. 10 and 11 has the speaker inbuilt in the mp3 player 10000 (not shown) on the back surface thereof.

The speaker of the mp3 player transmits sound through the housing 10006 via channels 10009 which exit on the upper surface 10008 of the housing 10006 against which an infant's head will rest.

Example 1

In one embodiment of the present invention there is shown an infant pabifying apparatus having an RP in the form of a housing which is in the form of a pad being substantially disc like in form (not shown) to which there is connected a speaker and associated power supply (both not shown). The speaker is configured to receive an auditory output signal via BLUETOOTH™ from a remote sound apparatus in the form of a smart phone such as an iPhone™ (not shown). The housing has a foam cover (not shown) against which the infant's head rests so as to not contact the housing/speaker directly, which would be uncomfortable.

The smart phone has a music playing application similar to the iPod™ application on the iPhone™ said application being configured to play one or more white noise sound tracks at the desired sound level. In use the housing is held in the hand of the adult so the speaker side of the housing is facing outwardly from the palm so as to be proximate an infant's head which can then be rested thereon.

Detailed Discussion of Ways to Alternate Implement the Invention

The receiving portion (RP) may come in a variety of different forms without departing from the scope of the present invention.

In one embodiment the RP may be in the form of a mitten.

In some embodiments the RP may be in the form of a fingerless glove.

In another embodiment the RP may be in the form of a strap which is attached to a housing.

Alternatively, the RP may fit within a strap in the form of a loop of elasticised material which can surround a person's hand or arm.

In yet another embodiment the RP may be in the form of a pad which can be handheld.

In some further embodiments the RP may be in the form of at least one sleeve, band or such like that can be worn on an arm, or over one or more fingers and/or thumb. For example in one possible embodiment the RP may be in the form of a ring which houses the sound system and is worn on a finger or thumb.

The RP may also be configured so that the sound system is positioned to not substantially interfere, in use, with the palm, and/or, thumb and fingers, of a user receiving tactile feedback: when moving to cradle, or when cradling, the infant's head.

In some embodiments RP may be in the form of a housing made from a sound permeable material, or configured to allow sound to travel from the auditory output device to the outer surface of the housing.

In one embodiment the sound system is positioned on the back hand side of the RP having regard to a plane through the hand within the RP. In some preferred embodiments the plane may be below the surfaces of the fingers/palm and thumb.

The auditory output device may come in a variety of different forms without departing from the scope of the present invention.

In other embodiments the auditory output device may be in the form of a speaker.

In some further embodiments the auditory output device may be in the form of a bone conduction device. A bone conduction device being a device configured to facilitate the conduction of sound to the inner ear through the bones of the skull.

The speaker of the sound system may be located in between the thumb and index finger and may be positioned so as to not project substantially above the surface of the fingers and thumb.

In one embodiment the white noise may be the sound of waves crashing.

In another embodiment the white noise may be the sound of rain on an iron roof.

In some further embodiments the white noise may be the sound produced by radio static.

In another embodiment the white noise may be the sound of a heart beat.

In some further embodiments, the white noise may be user selected from a plurality of white noise options.

In some embodiments the sound may be in the form of musical composition or a sample of one or more musical compositions. In some embodiments the musical composition may be classical music. For example, compositions by Mozart.

The sound system may come in a variety of different forms.

In one embodiment the sound system may include a heat sensitive switch which activates the system when heat is sensed within the RP and deactivates when no heat is detected within the RP.

In some embodiments the sound system may include a programmable logic unit (PLU).

The sound system may include an amplifier in some embodiments.

In one embodiment the sound system may be an Mp3 player or the like. One such an example is an iPod™. In some such embodiments the Mp3 player may include an inbuilt speaker.

In another embodiment the sound system may be a smart phone with a suitable software application to play recorded sounds. For example, the smart phone may be an iPhone™ which includes an iPod™ application and a suitable white noise audio track.

In further embodiments, the sound system is configured so as to produce a single safe audible output, that is optimised having regard to the need for the output to be both effective in calming the infant, but without any risk of damage to the infant's hearing.

In some embodiments the sound system may include a microphone connected to the PLU wherein the PLU is configured to analyse ambient noise received by the microphone and adjust the sound level within a safe range to help ensure sufficient detection of white noise by an infant. In some further embodiments the PLU may also select a particular type of white noise to be generated having regard to the ambient noise received by the microphone.

The sound permeable material of the RP and/or web element may be any number of known materials which are non-toxic and suitable for contact with an infant's skin without causing discomfort or irritation.

Ideally the sound permeable material may be washable, or if a disposal material such as paper based or synthetic material (easily recyclable).

In a preferred embodiment the RP may be made out of neoprene.

The material of the RP and/or web element may be washable.

In some embodiments the RP and/or web element may be made out of cloth. In some such embodiments the RP may also include padding. In one embodiment the padding may be a foam material.

In some embodiments the thickness of the RP and/or web element should such as to allow for sound permeation and tactile feedback from an infant's head. For example, if the RP is made of neoprene the thickness of the RP may generally be substantially 2 mm and not more than 5 mm in thickness.

In some preferred embodiments the RP and/or web element may include a pocket which houses the sound system to facilitate easy removal thereof to enable washing of the RP. The pocket may include a cushioning layer. The cushioning layer may also be made from a substantially sound permeable material and/or be adapted to allow for sound to permeate therethrough.

A material may be adapted to allow for sound to permeate therethrough in any number of ways without departing from the scope of the present invention. For example, the material may include one of more apertures or areas of reduced thickness.

In some embodiments the RP may be in the form of two sleeves respectively configured to receive a thumb and forefinger wherein said sleeves are bridged by at least one web element to which the sound system is attached.

In some further embodiments the apparatus may include one or more disposable or interchangeable outer layers of material thereon.

In additional embodiments the RP may include on the backhand side thereof one or more reinforcing elements which are configured to hold a user's hand in a correct cradling position. In general the correct cradling position is one in which the user's fingers, palm and thumb present a substantially open surface upon which an infant may rest their head.

Aspects of the present invention have been described by way of example only and it should be appreciated that modifications and additions may be made thereto without departing from the scope of the appended claims.

ADVANTAGES OF THE INVENTION

Thus embodiments may have one or more advantages over the prior art which may include:

The apparatus can be easily used.

The apparatus does not interfere with support and/or comfort of the infant's head when being cradled. The fact tactile feedback is received is important as this gives the parent comfort they are not being unduly rough with the head of the infant which is a risk if tactile feedback were masked. This can reduce the risk of dropping the infant while using the device, compared to using a pillow or white noise generating toy.

The apparatus can be worn easily. It can reduce suffocation risk associated with infants using pillows.

The apparatus is able (via the sound system when playing white noise (or similar sounds)) to soothe an infant and encourage sleep in most situations and with people other than the parent or close family members in regular contact with the infant. Thus, providing an ideal baby sitter aid.

The apparatus is easily transportable, compact and can be used when out and about on the move without the need for a cot or other bed.

Another advantage is that white noise is audible to the infant but inaudible to the user or others in the immediate vicinity due to the ability to position the speaker substantially adjacent an infant's ear. The same is not true of pillows and sound emitting toys which require sound to be emitted at a sufficient volume to travel any distance between the ear and the speaker.

What we claim is:

1. An infant pacifying apparatus, comprising:
   a member configured for receiving a hand of an adult cradling an infant, said member including a first receiving portion and a second receiving portion;
   a web element extending between said first receiving portion and said second receiving portion;
   a sound system attached to said web element, said sound system comprising a sound generator and associated power source; and
   an auditory output device associated with the sound system,
   wherein at least one of the sound system and the auditory output device are configured to enable the auditory output device to solely emit sound from the web element at a level which is audible to the adult cradling the infant but not audible to any other adult within a one meter radius of the adult, and wherein the web element is configured to be positioned on the hand of the adult cradling the infant such that the auditory output device is able to rest against the infant's ear.

2. The infant pacifying apparatus as claimed in claim 1, wherein at least one of the first and second receiving portions are configured to house:

the auditory output device; or the sound system and a sound output device;

in a manner which does not substantially interfere, in use, with a support and/or comfort of an infant's head.

3. The infant pacifying apparatus as claimed in claim 2, wherein at least one of the sound system and the auditory output device are configured to enable the auditory output device to produce sound at a level, which can be heard by the infant being cradled, yet cannot be heard by an adult outside a radius of 30 mm of the auditory output device.

4. The infant pacifying apparatus as claimed in claim 3, wherein the sound is produced at a level of 35-60dB to ensure it is at a safe level for the infant and not so loud as to be heard by the adult cradling the infant unless the infant is being held up close to the adult's face.

5. The infant pacifying apparatus as claimed in claim 4, wherein the sound is white noise.

6. The infant pacifying apparatus as claimed in claim 3, wherein the sound is white noise.

7. The infant pacifying apparatus as claimed in claim 2, wherein the sound is white noise.

8. The infant pacifying apparatus as claimed in claim 2, wherein the first and second receiving portions are configured so that the sound system is positioned to not substantially interfere, in use, with:

a palm; and/or, thumb and fingers; and/or an arm;

of a user receiving tactile feedback: when moving to cradle, or when cradling, the infant's head.

9. The infant pacifying apparatus as claimed in claim 1, wherein the first and second receiving portions are configured so that the sound system is positioned to not substantially interfere, in use, with:

a palm; and/or, thumb and fingers; and/or an arm;

of a user receiving tactile feedback: when moving to cradle, or when cradling, the infant's head.

10. The infant pacifying apparatus as claimed in claim 1, wherein said first receiving portion is a palm receiving portion configured to receive a palm of the hand and said second receiving portion is a thumb receiving portion configured to receive a thumb of the hand.

* * * * *